United States Patent [19]

Douvas et al.

[11] 4,168,707
[45] Sep. 25, 1979

[54] CONTROL APPARATUS FOR MICROSURGICAL INSTRUMENTS

[76] Inventors: Nicholas G. Douvas, 4200 N. Gratiot, Port Huron, Mich. 48060; Henry T. Dinelkamp, 200 W. Orchard Pl., Mt. Prospect, Ill. 60056

[21] Appl. No.: 806,161

[22] Filed: Jun. 13, 1977

[51] Int. Cl.² .................................. A61M 1/00
[52] U.S. Cl. .................................. 128/276; 128/230; 128/DIG. 13; 128/305; 250/573; 324/65 R; 73/725; 200/86.5
[58] Field of Search ............... 128/276, 277, 278, 305, 128/2 A, 230, DIG. 29, 214 E, 2.05 E, 2.05 F, DIG. 13; 73/725, 719, 702; 137/557; 141/95; 222/39; 116/114 PV; 338/42; 324/61 QS; 331/64, 65; 200/86.5, 5 R, 17 R, 17 B, 153 C; 250/573

[56] References Cited

U.S. PATENT DOCUMENTS

| | | | |
|---|---|---|---|
| 1,412,777 | 4/1922 | Crafton | 137/557 |
| 2,483,924 | 10/1949 | Moulinier | 128/278 |
| 2,671,268 | 3/1954 | Crawford | 200/86.5 |
| 2,807,012 | 9/1957 | Schwarz | 128/214 E |
| 2,828,379 | 3/1958 | Simonds et al. | 200/153 C |
| 2,911,606 | 11/1959 | Hoffman | 73/725 |
| 3,284,707 | 11/1966 | Clinton | 324/62 R |
| 3,563,090 | 2/1971 | Deltour | 128/214 E |
| 3,742,167 | 6/1973 | Muther | 200/86.5 |
| 3,753,199 | 8/1973 | Rice | 73/725 |
| 3,758,855 | 9/1973 | Meyer | 324/65 R |
| 3,799,702 | 3/1974 | Weishaar | 128/278 |
| 3,812,855 | 5/1974 | Banko | 128/2 A |
| 3,833,782 | 9/1974 | Bartel | 200/86.5 |
| 3,882,872 | 5/1975 | Douvas et al. | 128/305 |
| 3,920,014 | 11/1975 | Banko | 128/230 |
| 3,980,848 | 9/1976 | Schulz et al. | 200/153 C |
| 3,980,849 | 9/1976 | Straihammer | 200/153 C |

FOREIGN PATENT DOCUMENTS 2258870 8/1975 France .................................. 128/230

*Primary Examiner*—Robert W. Michell
*Assistant Examiner*—Arthur S. Rose

[57] ABSTRACT

An automated electronic microsurgical control system is disclosed which is capable of performing the various aspiration functions customarily performed manually by a surgical assistant. The system is entirely subservient to the surgeon's foot control unit which is adapted to control seven different surgical functions. In addition, the electronic control system is designed to communicate audibly with the surgeon regarding actual fluid flow and the build-up of vacuum pressure in the aspiration lines connected to the microsurgical cutting instrument, thus permitting the surgeon to audibly ascertain complete information as to the actual activity within the aspiration line without requiring him to take his eyes from the operating microscope.

21 Claims, 17 Drawing Figures

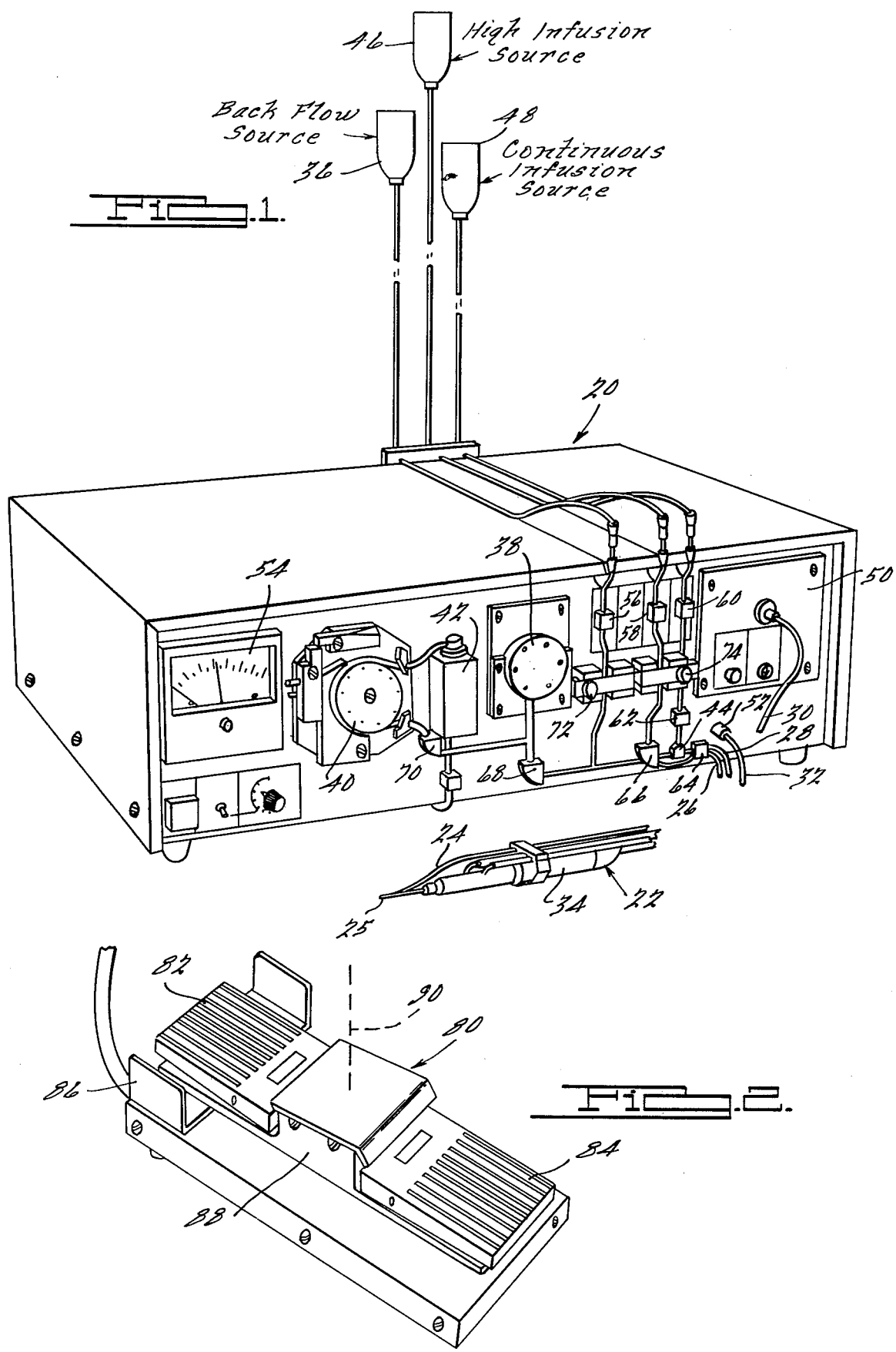

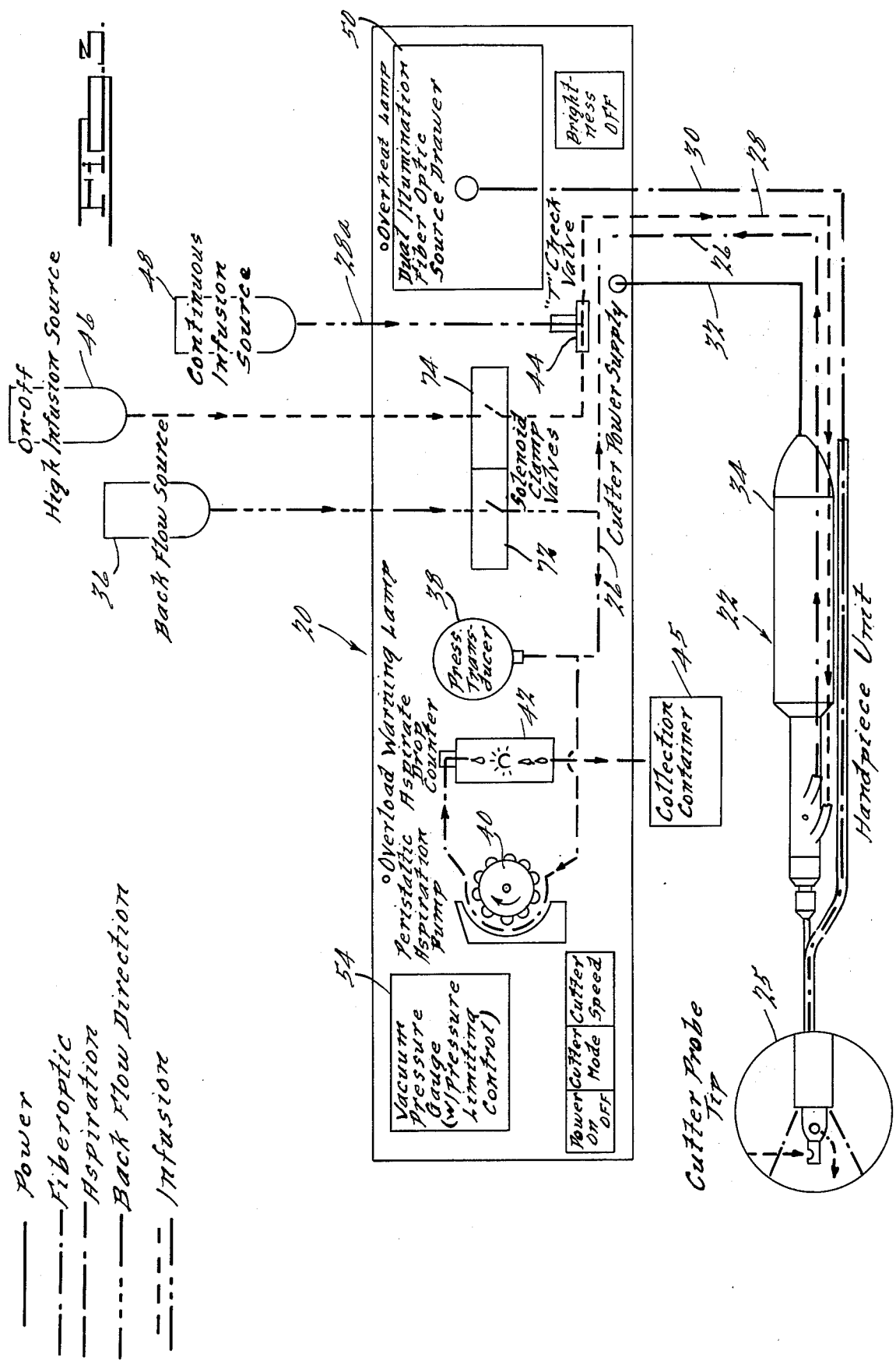

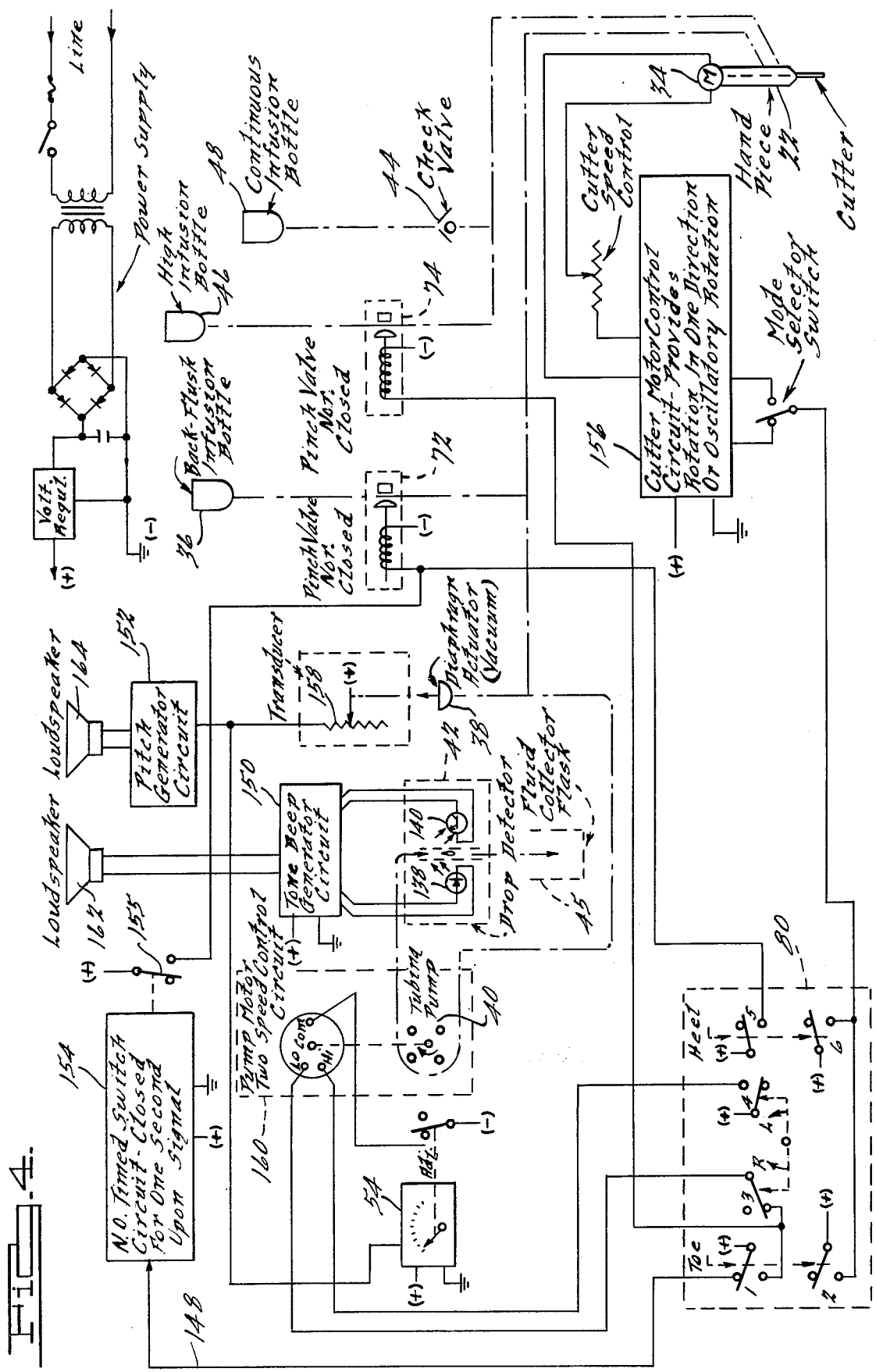

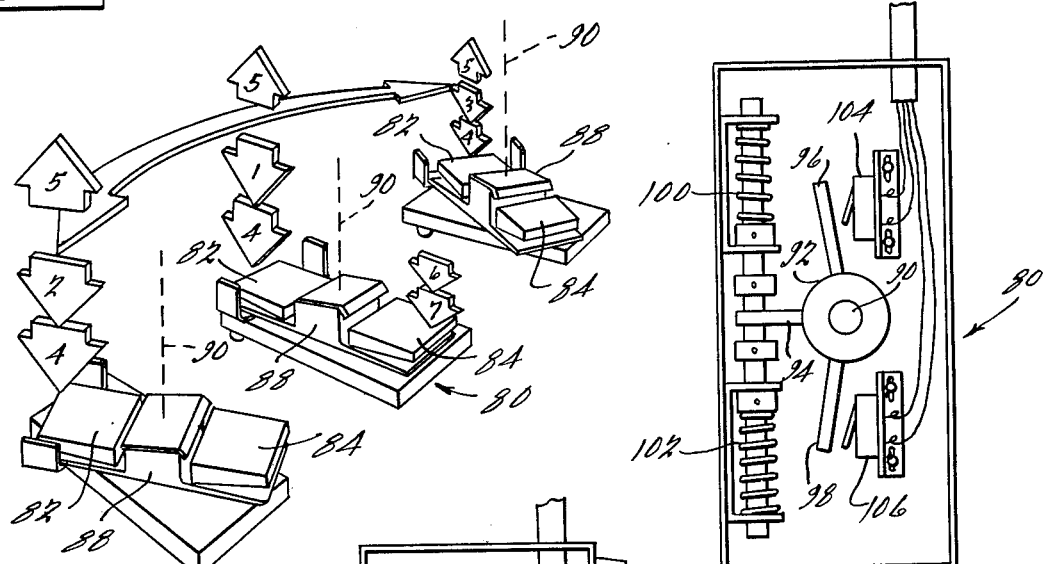
FIG. 5.
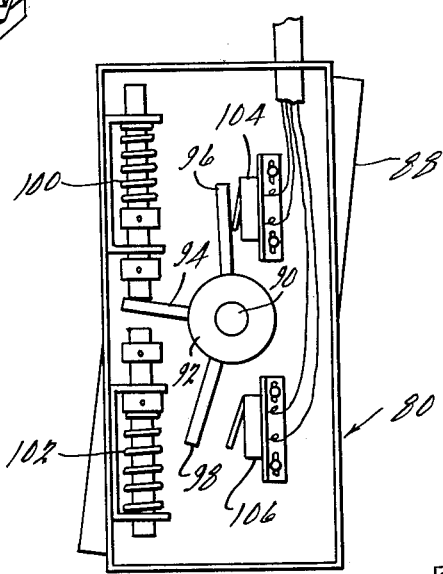
FIG. 6a.
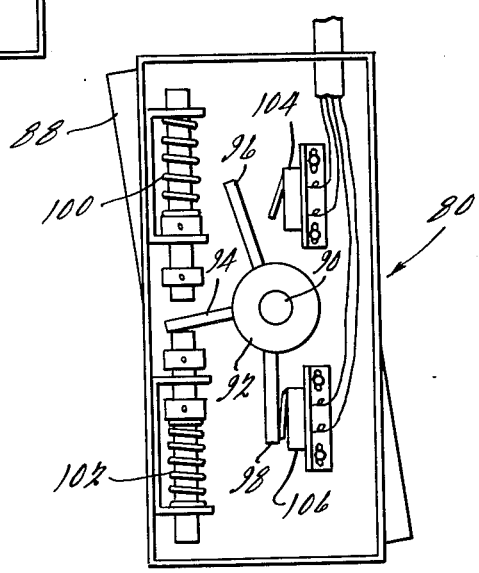
FIG. 6b.
FIG. 6c.

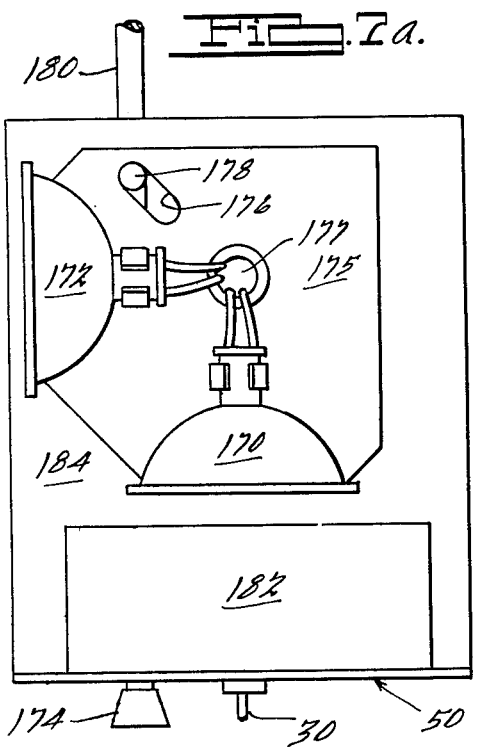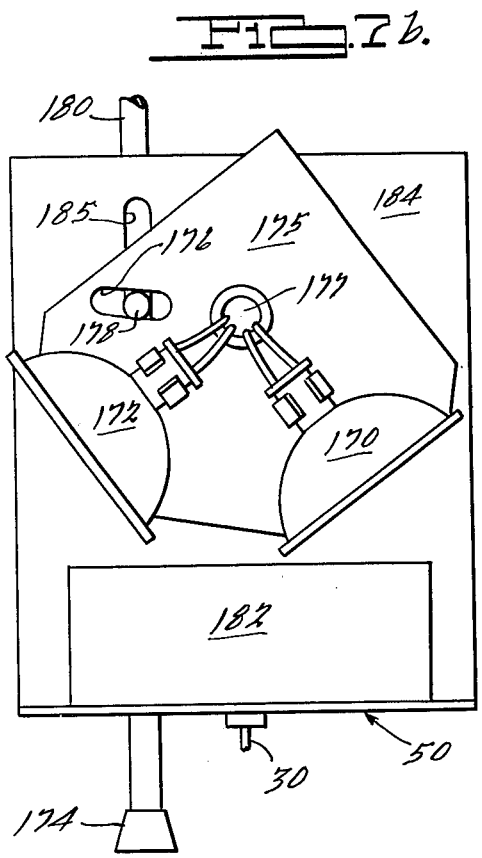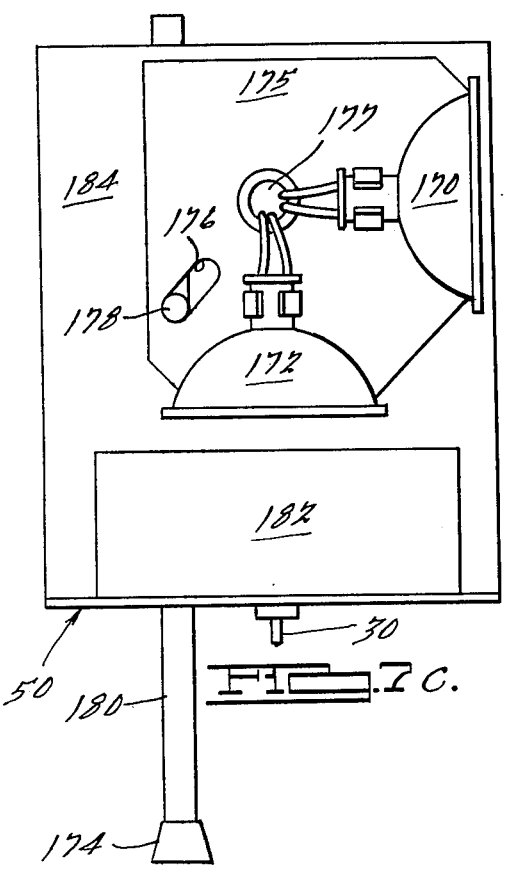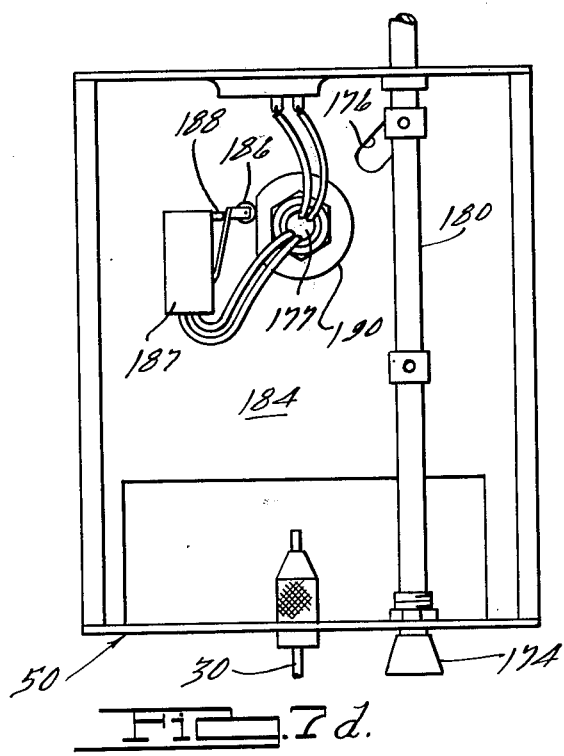

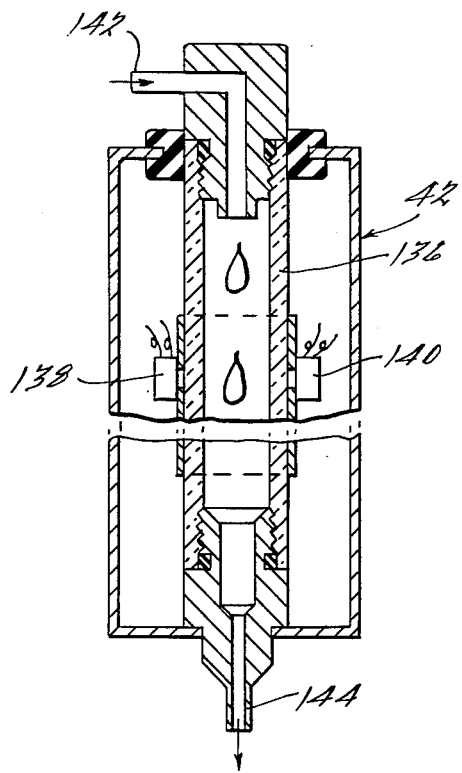
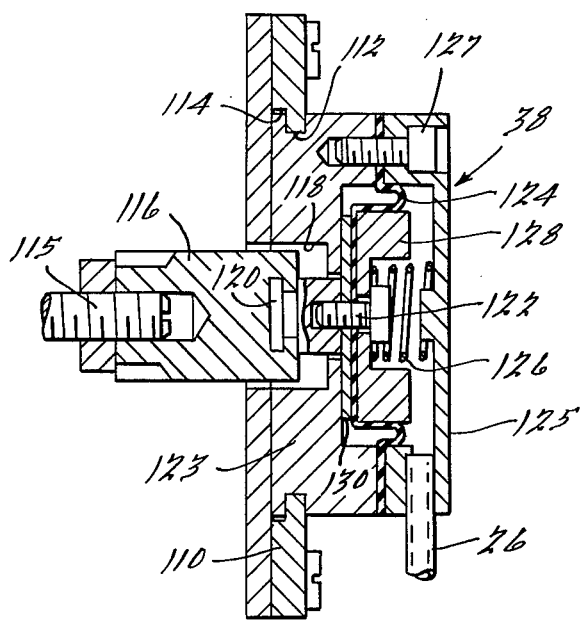
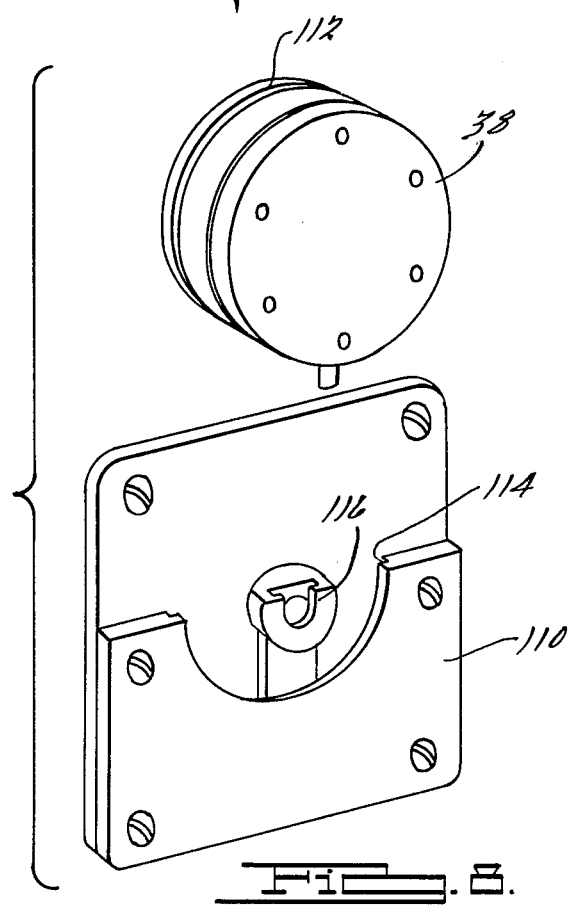
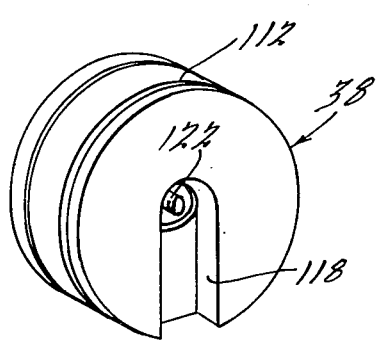
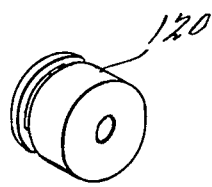

CONTROL APPARATUS FOR MICROSURGICAL INSTRUMENTS

BACKGROUND AND SUMMARY OF THE INVENTION

The present invention relates to electronic control apparatus for microsurgical instruments and in particular to an electronic control system that is adapted for use in intraocular surgery to control in accordance with commands received from a surgeon's foot control unit the various aspiration functions normally performed manually by a surgical assistant.

A competent eye surgical assistant provides the manual functions of: (1) aspiration, (2) reverse injection of "backflush," (3) proprioceptive feedback determination of aspiration resistance, and (4) balancing aspiration volume with infusion volume. Ideally an automated system should provide equal control and information to the surgeon. In addition, it should not be necessary for the surgeon to take his eyes from the operating microscope in order to turn and look at console dials. Moreover, console technical assistance requirements should be minimal and not vital to the surgical outcome of a procedure.

The present invention satisfies all of these criteria by providing an electronic control system that is entirely subservient to a multi-position foot control switch operated by the surgeon. The control system utilizes the safety of gravity flow infusion pressure determined by bottle height above the patient's eye. A basic low infusion pressure bottle is used in conjunction with a high infusion pressure bottle and an intermediate infusion pressure bottle is used for backflow or "backflushing" of the aspiration tubing. A peristaltic suction pump supplies aspiration and is calibrated for a low and a high suction rate that does not exceed the infusion volume capabilities of the system.

Infusion pressure and aspiration rate are controlled by the surgeon in accordance with the position of the foot control unit. The low infusion pressure bottle is always opened and provides a minimum amount of infusion pressure. The high infusion bottle is activated in conjunction with the low suction rate by initial depression of the foot switch by the surgeon. Rotation of the foot switch to the left in conjunction with the above initial switch depression initiates the high suction rate for more rapid aspiration. Rotation of the foot switch to the right stops the suction pump and limits the vacuum force to the amount in existence within the system, so as to permit the surgeon to sustain a minimal tissue impaction in the cutting aperture prior to activation of the cutter by further foot depression. Further depression of the toe switch in all three swivel positions activates cutting. Release of foot switch depression at any time immediately cancels all suction forces within the system without lowering intraocular pressure.

Control over the infusion pressure and aspiration rate provides the surgeon with several important functional capabilities. As noted, the system provides the surgeon with the ability to sustain a minimal amount of suction for tissue impaction and cutting only of the desired tissue without subsequent inadvertent tissue aspiration. In addition, pulsing of the suction pump by intermittent swiveling of the foot while maintaining initial toe depression permits the surgeon to test the aspirate and determine what tissue is being impacted or aspirated into the cutting aperture prior to cutting. Most importantly, the surgeon is provided with the capability of controlling the rate and volume of both aspiration and infusion which permits the surgeon to maintain a pressurized ocular globe throughout the surgical procedure. Moreover, as previously noted, the heights of the infusion bottles above the patient's eye, which determine the intraocular pressure in the absence of aspiration, and the calibration of the peristaltic suction pump, are selected to permit easy maintenance of the proper pressure within the eyeball.

Reverse injection of "backflush" ability to reflux unwanted aspirate from the cutting aperture is accomplished by heel depression of the rear foot switch. Further switch depression of the rear foot switch combines reverse injection with cutting.

In the common prior art practice, the information derived proprioceptively by the surgical assistant through manual aspiration, was communicated to the surgeon verbally. In accordance with the present invention the same information is provided to the surgeon by an audible sound beep of varying rapidity. Specifically, the slower rate of flow of aspirate the less frequent the sound beeps, and the faster the flow rate the more frequent the sound beeps. The audible flow device basically comprises a drip counter that is attached to the discharge side of the peristaltic pump. A photocell and a light transmitter are positioned on opposite sides of a drip tube so that drops of fluid or tissue containing fluid which fall through the transparent drip tube interrupt the light beam from the transmitter to the photo-detector. Each time this occurs, the photoelectric system triggers a "beep" tone. The faster the drops fall, the faster the beeps occur, thus providing the surgeon with a quantitative indication of the number of drops of fluid being drawn from the eye. If there is no fluid flow, no beep sound is generated.

In order to inform the surgeon when there is resistance to aspiration, the present control system is adapted to generate a different audible sound when a negative or vacuum pressure exists in the aspiration line. The sound produced is continuous and of increasing pitch as the vacuum pressure in the aspiration line increases. If the surgeon has even average tone-pitch recognition, he can readily determine the approximate suction pressure without removing his eyes from the operating microscope to view a meter. The continuous audible signal is generated by a transducer that is hydraulically connected to the system and mechanically coupled to an electrical transducer located inside the console. The output of the electrical transducer is fed through appropriate circuitry to provide a meter indication of the suction pressure as well as activating a tone signal generator which provides the audible signal.

Thus, the interplay of the two distinctive sounds and their frequencies generated by the present control system imparts first hand knowledge to the surgeon as to the actual activity within the aspiration lines, and not merely information that the suction pump is running. As is well known to those skilled in the art, a running pump does not necessarily mean that fluid flow is resulting. Rather, a running pump may be resulting in vacuum build-up unbeknown to the surgeon until a preselected maximum suction limit is achieved automatically deactivating the pump. As noted previously, it is important for the surgeon to have knowledge of initial vacuum build-up in order to ascertain that tissue impaction is being achieved. In the absence of vacuum build-up, the present control system will generate a repeating beep sound indicating to the surgeon the passage of fluid into the collection bottle.

Importantly, it will be seen that, because of the possibility of backflow in a system of the present type, the pressure transducer utilized in the present invention, along with the total harness and tubing system, can be readily sterilized. When the system is prepared for surgery, the sterilized transducer is easily inserted into a receptacle located on the front panel of the console, and thereby automatically coupled mechanically to the electrical transducer located inside the console.

The present control system is also equipped with a halogen light source to provide light to a fiberoptic cord that emits light at the distal end of the cutter probe tip when inserted into the eye. Novel means are provided for rapidly switching lamps in the event of a lamp burnout. In particular, if a lamp burnout should occur during surgery, a new lamp is rotated into position by pulling out a knob located on the front panel of the control unit. When the knob is pulled outwardly, a carousel inside of the unit rotates a spare lamp into proper alignment with the end of the fiberoptic cord and electrical power is automatically switched from the main lamp to the spare lamp by means of a switch that is actuated by the rotation of a cam connected to the axle of the carousel.

Further objects and advantages of the present invention will become apparent from a reading of the detailed description of the preferred embodiment which makes reference to the following set of drawings in which:

BRIEF DESCRIPTION OF THE DRAWINGS

FIG. 1 is a somewhat diagrammatic perspective view of an electronic microsurgical control unit according to the present invention;

FIG. 2 is a perspective view of a foot switch control unit according to the present invention;

FIG. 3 is a flow diagram of the control unit shown in FIG. 1;

FIG. 4 is a block diagram of the electronic control unit shown in FIG. 1;

FIG. 5 is a diagram illustrating the seven positions of the foot switch control unit shown in FIG. 2;

FIGS. 6a-6c are various views of the underside of the foot switch control unit illustrating the switch mechanism contained therein;

FIGS. 7a-7d illustrate the dual fiberoptic light sources and the manner in which a replacement bulb is rotated into position in the event of a primary bulb failure;

FIG. 8 is an illustration of the pressure transducer according to the present invention and the receptacle therefor located on the front panel of the control unit shown in FIG. 1;

FIG. 9a is a rear view of the pressure transducer illustrated in FIG. 8;

FIG. 9b is an illustration of the coupling device that mechanically connects the pressure transducer to the electrical transducer inside the console;

FIG. 10 is a sectional view of the pressure transducer when inserted within the receptacle shown in FIG. 8; and FIG. 11 is a sectional view of the aspirate drip counter according to the present invention.

DETAILED DESCRIPTION OF THE PREFERRED EMBODIMENT

Referring to FIG. 1, a plan view of the electronic control unit 20 according to the present invention is shown. The electronic control unit 20 is particularly suited to perform automatically the infusion and aspiration functions required during intraocular surgery which are customarily performed by a surgical assistant. To perform intraocular surgery, the surgeon requires a handpiece unit 22 that is capable of performing the functions of cutting, aspiration, and infusion. An intraocular microsurgical handpiece unit of this type is described in detail in U.S. Pat. Nos. 3,990,453 and 3,882,872 issued to the inventors of the present invention. Present generation handpiece units 22 of the type contemplated herein and illustrated in the figures also contain a fiberoptic light sleeve 24 that is adapted to provide a source of light at the cutting aperture 25 of the handpiece unit 22. Thus, a multi-functional intraocular microsurgical handpiece unit 22 of the type described will have four lines leading therefrom: (1) an aspiration line 26, (2) an infusion line 28, (3) a fiberoptic cord 30, and (4) a power line 32 for the cutter motor 34. The aspiration line 26 is hydraulically coupled to a backflow source 36, a pressure transducer 38, and through a peristaltic pump 40 and an aspirate drip detector 42 to a collection container (not shown). The infusion line 28 is split at a T-joint 44 and hydraulically connected to a high infusion source 46 and a continuous infusion source 48. The fiberoptic cord 30 is connected to the dual light source drawer 50 and the power line 32 is simply connected to an electrical receptacle 52 on the front panel of the control unit 20. A vacuum pressure gauge 54 is also provided on the front panel of the control unit 20 which provides a visual read-out of the amount of pressure existing in the aspiration lines, and also provides an adjustable vacuum pressure high limit switch.

The total harness and tubing system—including the pressure transducer 38 to be subsequently described in greater deatil—is designed to be readily removable from the control unit 20 to permit complete sterilization of the harness. As noted previously, because it is sometimes necessary during surgery to backflow aspirate previously drawn from the eye, it is highly desirable that the pressure transducer 38, which is hydraulically connected to the aspirating system, be sterilizable along with the entire tubing system. As will also be explained more fully in connection with the description of FIGS. 8-10, the pressure transducer 38 is specially adapted to be readily coupled mechanically to the electrical transducer located inside the control console 20, to facilitate easy removal of the pressure transducer 38 for sterilization purposes. The entire tubing system is also readily disconnected from the control unit 20 simply by unhooking the tubing from the various retainer clips 56-70 and opening the two solenoid clamp valves 72 and 74, removing the aspirate line from the peristaltic pump 40 and disconnecting the line from the aspirate drip detector 42. Thus, it can be seen that the present control system is designed to permit ready sterilization of all component parts thereof that communicate with fluid which may enter the eye during surgery.

Referring now to FIG. 2, a foot switch control unit 80 according to the present invention is shown. The foot switch control unit 80 is electrically connected to the electronic control console 20 illustrated in FIG. 1 and is adapted to control the various functions performed by the console unit 20. The foot unit 80 comprises a pair of three-position pedal switches 82 and 84 that are adapted to be selectively depressed by the toe and heel, respectively, of the surgeon. Depression of the pedal switches 82 and 84 to their initial depressed position requires a relatively small amount of foot pressure. Depression of the pedal switches 82 and 84 to their second depressed position, however, requires a significantly greater amount of foot pressure. Thus the surgeon is readily able to control the position of the pedal switches 82 and 84 without possessing an inordinate amount of dexterity in his foot. Foot pedal switches of the described type are commercially available, the particular pedal switch utilized in the preferred embodiment being purchased from Line Master Switch Corporation, their catalog no. T52-s.

The pedal switch assembly 88 has fastened thereto a U-shaped bracket 85 adjacent the toe pedal switch 82 which permits the surgeon to pivot the pedal switch assembly 88 either left or right about its centralized axis 90. Thus, the combination of the three-position toe and heel foot pedal switches 82 and 84 and the pivoting action of the pedal switch assembly 88 provides the foot switch control unit 80 with a possibility of more than the required seven switch positions. With particular reference to FIG. 5, the seven switch positions utilized in the preferred embodiment are diagrammatically illustrated. The functions performed by the control system in each of the seven identified positions are as follows:

1. Initial depression of the toe pedal 82 activates the high infusion bottle 46 in conjunction with a low suction rate.

2. Pivoting of the foot switch assembly 88 to the surgeon's left in conjunction with the initial toe pedal 82 depression initiates the high suction rate for more rapid aspiration with continued high infusion.

3. Pivoting of the foot switch assembly 88 to the surgeon's right in conjunction with the initial toe pedal 82 depression described in No. 1 stops the vacuum pump 40 and sustains the vacuum pressure existing within the aspiration line 26 while the high infusion bottle 46 remains open. This permits the surgeon to retain a desired minimal tissue impaction at the cutting aperture prior to cutting.

4. Further depression of the toe pedal 82 in any position combines cutting activation with any of the three functions described in the three preceding foot pedal positions.

5. Release of toe pedal 82 depression at any time immediately stops cutting activity and cancels all suction forces within the aspiration system without lowering intraocular pressure.

6. Initial depression of the heel pedal 84 activates a reverse injection or "backflush" into the aspiration line 26.

7. Further depression of the heel pedal 84 combines cutting activation with the reverse injection or "backflush" described in No. 6.

Looking now to FIGS. 6a-6c, the pivotal switching action of the foot switch control unit 80 is shown. The underside of the foot switch control unit 80 is seen to comprise a rotating hub member 92 that pivots about axis 90. Connected to hub 92 are three radially extending arms 94, 96, and 98. Radial arm 94 is normally positioned between return springs 100 and 102. Radial arms 96 and 98 are positioned relative to switches 104 and 106 such that when the foot pedal assembly is pivoted to the surgeon's left, as illustrated in FIG. 6b, radial arm 96 will actuate switch 104, and when the foot pedal assembly 88 is pivoted to the surgeon's right, as illustrated in FIG. 6c, radial arm 98 will actuate switch 106. It will be noted, that when the foot pedal assembly 88 is pivoted as shown in FIG. 6b, radial arm 94 compresses spring 100 thereby causing spring 100 to exert a bias force on radial arm 94, and hence on the foot pedal assembly 88, tending to return radial arm 94 to its original position illustrated in FIG. 6a. Similarly, when the foot pedal assembly 88 is pivoted as shown in FIG. 6c, radial arm 94 compresses spring 102 causing it to exert a bias force tending to return radial arm 94 to its original position. Thus, it can be seen that whenever the surgeon's foot is removed from the foot switch control unit 80, the pedal assembly 88 will automatically return to its neutral position.

Referring now to FIG. 3, a flow diagram for the present microsurgical control unit 20 is shown. As noted previously, the electronic control unit 20 controls, in accordance with instructions received from the foot switch control unit 80, the rates of aspiration and infusion at the probe tip 25 of the microsurgical handpiece unit 22, as well as the activation and speed of the cutter motor 34. It is of vital importance during intraocular surgery to maintain the proper amount of pressure within the eyeball at all times. Absent the maintenance of appropriate intraocular pressure during surgery, the eyeball could collapse. Accordingly, as fluid and tissue are being aspirated, an equal volume of fluid must be injected into the eye. Infusion pressure is provided by the present invention utilizing the safety of gravity flow. In particular, infusion pressures are determined by the heights of the infusion bottles 46 and 48 above the patient's eye. The high infusion bottle 46 is typically placed at a height of approximately 1 meter above the eye and the continuous infusion bottle is typically positioned approximately ½ meter above the eye, although these heights may vary considerably. An intermediate infusion pressure bottle 36 is used for backflow or "backflushing" of the aspiration line and is typically placed approximately ¾ meter above the eye.

The continuous infusion source 48 as the name implies is on throughout the duration of the surgery and establishes a minimum infusion pressure at the cutter probe tip 25. Fluid flow from the continuous infusion bottle 48 is directed to the handpiece unit 22 through a "T" check valve 44 which acts as a one-way valve preventing higher pressure fluid from the high pressure infusion bottle 46 from flowing up infusion line 28a into the continuous infusion bottle 48. Fluid flow from the high infusion bottle 46 to the handpiece unit 22 is controlled by a solenoid clamp valve 74 which is opened whenever the toe switch pedal on the foot control unit is depressed.

Suction pressure is provided by a peristaltic pump 40. This type of pump avoids contamination of the aspiration line 26 by maintaining the line continually closed. The peristaltic pump 40 is calibrated to provide a low and a high suction rate that does not exceed the infusion volume capabilities of the system. In this manner, the maintenance of the appropriate intraocular pressure is facilitated. When the suction pump 40 is activated, aspirate is drawn from the patient's eye through the cutter probe tip 25 and into the aspiration line 26 hydraulically connected to the handpiece unit 22. The peristaltic pump 40 then pumps the aspirate through a drop detector 42 and into a collection container 45. The aspirate drop detector 42 essentially comprises a photo-electric detector that is adapted to activate a tone beep generator circuit (see FIG. 4) whenever a drop of aspirate passes through a drip tube. In this manner, the surgeon is provided with a distinct audible sound from which he can readily determine the rate at which the aspirate is being drawn from the patient's eye.

In addition to information relating to the rate of aspiration, it is also desirable for the surgeon to be informed as to the build-up of negative or vacuum pressure in the aspiration line 26. Simply because the pump 40 is running does not necessarily mean that flow is resulting. Resistance to aspiration, which can be caused by many different factors, may result in a build-up of vacuum pressure in the aspiration line 26. If such a situation occurs, it is important that the surgeon be immediately informed rather than first discovering the condition when a preselected maximum suction limit is attained deactivating the pump. Moreover, it is equally important prior to cutting for the surgeon to be able to determine when initial vacuum build-up occurs in order to ascertain that tissue impaction in the cutting aperture is being achieved. The present invention provides this information proprioceptively to the surgeon through the use of a pressure transducer that is hydraulically coupled to the aspiration line 26, and mechanically coupled to an electrical transducer located inside the control console which drives a pitch generator circuit (see FIG. 4). For a constant line pressure, a continuous fixed-pitch audible sound is generated. However, as the pressure within the aspiration line 26 increases, the pitch of the continuous audible sound increases. Conversely, as the pressure within the aspiration line 26 decreases, the pitch of the continuous audible sound decreases accordingly. Thus, it can be seen that even a surgeon of average pitch perception can readily approximate the level of suction pressure existing in the aspiration line 26 without removing his eyes from the operating microscope.

When combined with the distinct beep sound generated by the tone beep generator in response to the flow of aspirate, the continuous variable-pitch sound generated by the pressure transducer 38 and its associated circuitry imparts to the surgeon complete first-hand knowledge regarding the actual activity within the aspiration line 26. Significantly, this information is provided proprioceptively without requiring the surgeon to divert his attention from the operating microscope.

As noted previously, an intermediate infusion pressure bottle 36 is provided as a backflow source and is used to "backflush" the aspiration line 26 to cause unwanted aspirate from the cutting aperture to be reverse injected into the eye. The backflow source 36 is controlled by a solenoid clamp valve 72 that is activated in response to commands received from the surgeon's foot control unit. Specifically, in the preferred embodiment, backflow pressure is introduced into the aspiration line 26 whenever the heel pedal switch of the foot control unit is initially depressed. In addition, further depression of the heel pedal switch will combine cutting activation with reverse injection to allow further cutting of previously aspirated tissue which may have been creating resistance in the aspiration line 26. As will subsequently be discussed in greater detail, the solenoid clamp valve 72 controlling the backflow source 36 is also momentarily cycled whenever depression of the toe pedal switch is released in order to cancel all suction forces in the aspiration line 26.

Due to the fact that it may be necessary during surgery to reverse inject a significant amount of aspirate into the eye, the desirability of being able to sterilize the pressure transducer 38 along with the entire tubing harness becomes readily apparent. The pressure transducer 38 utilized in the present invention is specially designed to permit sterilization. With particular reference to FIG. 8, the pressure transducer 38 is adapted to be mechanically coupled to the electrical transducer located inside the control console simply by inserting the transducer 38 into the "holster-like" receptacle 110 located on the front panel of the console. The transducer 38 has a circumferential groove 112 formed therein that fits into a circular lip 114 in the receptacle 110. As the transducer 38 is dropped into place, the plunger 116 protruding from a hole in the front panel of the console is guided into a slotted recess 118 formed in the backside of the transducer 38, as shown in FIG. 9a. When the transducer 38 is completely inserted into the receptacle 110, the plunger 116 engages the retainer nut 120, illustrated in FIG. 9b, which is threaded onto the exposed shaft 122 on the backside of the transducer 38 at the apex of the recess 118.

Looking now to FIG. 10, a detailed sectional view of the pressure transducer 38 when inserted into the receptacle 110 fastened to the front panel of the control console is shown. The pressure transducer 38 comprises a diaphragm 124 that is hermetically sealed about its periphery by a pair of outer housing members 123 and 125 that are bolted together by a set of bolts 127. A return spring 126 is positioned on the inlet side of the diaphragm 124 between outer housing member 125 and a retainer ring 128. The spring retainer ring 128 is in turn secured to the diaphragm 124 by means of a bolt 122 whose shaft extends through a hole in the diaphragm 124 and is threaded to the retainer nut 120. A washer 130 is inserted between the diaphragm 124 and the retainer nut 120 to seal the hole in the diaphragm 124. As can readily be seen from the drawing, when the pressure transducer 38 is inserted into the receptacle 110, the retainer nut 120 engages the plunger 116 which is mechanically coupled to a linkage 115 from the electrical transducer (not shown). As suction pressure in the aspiration line 26 increases, the diaphragm 124 is moved eastwardly, relative to FIG. 10, against the bias of spring 126 causing the retainer nut 120 to withdraw the plunger 116 from within the front panel of the console. The movement of the plunger 116 causes a resistance change in the electrical transducer which in turn increases the pitch of the continuous audible sound generated by the pitch generator circuit (see FIG. 4). Similarly, as suction pressure in the aspiration line 26 diminishes, the return spring 126 will move the diaphragm 124 westwardly, relative to the figure, thereby retracting the plunger 116 and causing a decrease in the pitch of the continuous audible sound.

Thus, it can be seen that the pressure transducer 38 disclosed herein is designed to be automatically coupled to the electronic control unit simply by inserting the transducer 38 into the receptacle 110 located on the front panel of the console. Consequently, the pressure transducer 38 can be just as readily disconnected, along with the entire tubing harness, from the electronic control unit to permit complete sterilization of the tubing system, including the pressure transducer 38 which is hydraulically coupled to the aspiration line 26, prior to surgery.

Referring now to FIG. 4, an electrical block diagram of the automatic microsurgical control system according to the present invention is shown. As the diagram graphically illustrates, the operation of the entire system is under the complete control of the foot control unit 80. The foot control unit 80 comprises a pair of dual-position double-pole switches (1-2 and 5-6)—the toe and heel foot pedal switches—and a pair of double-pole single-throw switches (3 and 4)—the two switches located on the underside of the foot control unit 80 (see FIGS. 6a-6c). When the toe pedal switch is initially depressed, switch (1) is closed and power is applied to normally closed pinch valve 74, thereby opening the valve and permitting flow from the high infusion bottle 46. In addition, power is also applied through normally closed switch (3) to the LO-speed terminal of the two-speed pump motor control circuit 160, thereby activating the peristaltic pump 40. If the foot pedal assembly is pivoted to the left, closing switch (4), and the initial toe pedal depression is maintained, power will also be applied through switch (4) to the HI-speed terminal of the two-speed pump motor control circuit 160, thereby increasing the suction rate of the peristaltic pump 40. Similarly, if the foot pedal assembly is pivoted to the right, opening switches (3) and (4), power will be removed from the pump motor control circuit 160, thereby deactivating the vacuum pump 40 and sustaining the vacuum pressure existing within the aspiration line. Since initial toe pedal depression is also maintained, the high infusion bottle 46 will remain open. As previously noted, this position permits the surgeon to retain a desired minimal tissue impaction in the cutting aperture prior to cutting.

Any time the toe pedal switch is fully depressed, closing switch (2), power is applied through the mode select switch to the cutter motor control circuit 156, thereby activating the cutter motor 34. The cutter motor control circuit 156 is adapted to control in accordance with the position of the mode selector switch, the mode of operation of the cutter motor 34. In particular, the cutter motor control circuit 156 will cause the cutter motor 34 to either rotate in one direction or rotate in an oscillatory manner. The rotational speed of the cutter motor 34 in either mode can of course be varied simply by adjusting the setting of the cutter speed control.

Importantly, it will be noted that whenever toe pedal depression is released, thereby toggling switch (1) and closing pinch valve 74, a signal pulse is provided on line 148 to the normally opened timed switch circuit 154, which controls the actuation of switch 155. Upon receipt of a signal pulse on line 148, the timed switch circuit 154 is adapted to momentarily close switch 155 for approximately a one second interval, which in turn causes the normally closed pinch valve 72 to open for a corresponding time period. The relatively brief cycling of pinch valve 72 permits the infusion pressure from the backflush infusion bottle 36 to cancel the residual suction pressure existing in the aspiration line after the suction pump 40 is turned off. If the suction pump 40 was merely stopped and pinch valve 72 not cycled, the residual suction pressure in the aspiration line could cause continued unwanted fluid aspiration and tissue impaction. Note, that prior to cutting, the existence of a certain amount of suction in the aspiration line is desirable in order to cause the minimal tissue impaction in the cutting aperture. However, it is intended that this condition be provided by position No. 3 of the foot control unit (see FIG. 5) from which position cutting is readily initiated, and not when depression of the toe pedal switch is completely released. The top of the central portion 88 of the foot switch assembly is a smooth-surfaced rest for the surgeon's foot. In the operation of the unit the surgeon need never remove his foot from the rest, and merely depresses the front or rear pedals and swivels his foot on the rest as required. The different functions assigned to the various positions of the foot control unit in the preferred embodiment are logically related in a manner with which the surgeon can readily become familiar. Release of depression of the toe pedal switch causes a complete cessation of activity, including the cancellation of all residual suction forces in the aspiration line. Thus, the necessity of momentarily cycling pinch valve 72 when toe pedal depression is released can be appreciated. Appropriate intraocular pressure is maintained in this position by virtue of the infusion pressure supplied by the continuous infusion bottle 48.

Initial depression of the heel pedal switch closes switch (5) and applies power to the normally closed pinch valve 72, thereby opening the valve and permitting the introduction of infusion pressure into the aspiration line from the backflush infusion bottle 36. Further depression of the heel pedal switch closes switch (6) activates the cutting motor 34 to combine cutting action with the reverse injection.

Proprioceptive feedback information is provided to the surgeon by means of a tone beep generator circuit 150, a pitch generator circuit 152, and a pair of loudspeakers, 162 and 164 respectively. The pitch generator circuit 152 is adapted to produce a continuous whining sound through loudspeaker 164 whose pitch varies in accordance with the resistance of an electrical transducer 158. The resistance of electrical transducer 152 is varied in accordance with the movement of the diaphragm actuator 38 which is in turn controlled by the suction force in the aspiration line. Thus, it can be seen that the pitch of the continuous sound generated by the pitch generator circuit 152 through loudspeaker 164 is directly related to the amount of suction force in the aspiration line.

The tone beep generator circuit 150 is adapted to produce a beep sound whenever a drop of aspirate passes through the drop detector 42. With additional reference to FIG. 11, the drop detector 42 is adapted to have its inlet tube 142 connected to the output of the peristaltic pump 40 and its outlet tube 144 connected to a fluid collector 45. The drop detector 42 essentially comprises a transparent glass drip tube 136 having mounted on opposing sidewalls thereof a light emitting diode (LED) 138 and a phototransistor 140. The LED 138 and phototransistor 140 are positioned so that drops of fluid passing through the drip tube 136 will interrupt the beam of light transmitted from the LED 138 to the phototransistor 140. Each time the light beam is interrupted by a drop of fluid, the tone beep generator circuit 150 produces a beep sound through loudspeaker 162. Accordingly, it can be seen that the frequency at which the beep sounds are generated by the tone beep generator circuit 150 through loudspeaker 162 is directly related to the amount of fluid flow through the aspiration line.

Looking finally to FIGS. 7a-7d, the novel dual halogen light source drawer 50 is shown. The drawer 50 is located on the right of the control console (see FIG. 1) and contains a primary halogen light source 170 and a replacement halogen light source 172 that provide light to the fiberoptic cord 30 which emits light at the distal end of the cutter probe tip when inserted into the eye. Since the surgeon is dependent upon the light emitted from the cutter probe tip, the ability to quickly replace a burned out lamp is readily apparent. The present invention provides this capability by mounting two halogen lamps 170 and 172 on a turret or carousel 175. The lamps 170 and 172 are mounted so as to be directed at a right angle relative to one another. In the normal position of the carousel 175, the primary halogen lamp 170 is pointed directly toward the end of the fiberoptic cord 30. A deflector shield 182 is provided to contain the light emitted by the light source 170. In the event of a failure of lamp 170, replacement lamp 172 is rotated in the position previously occupied by lamp 170 simply by pulling out the knob 174 located on the front of the drawer 50. Knob 174 is fastened to the end of a rod 180 which has affixed thereto toward the opposite end of the rod 180 a guide pin 178 that extends through a longitudinal slot 185 in the base 184 and through an oblong slot 176 in the carousel 175. As the rod 180 is withdrawn from the drawer 50, as illustrated succesively in FIGS. 7a-7c, the guide pin 178 travels the length of slot 185 causing the carousel to rotate 90° as shown, thus positioning the replacement halogen lamp 172 directly in front of the end of the fiberoptic cord 30. With particular reference to FIG. 7d, as the carousel 175 is rotated about its axis 177, a cam wheel 190 fastened to the carousel 175 also rotates (counterclockwise relative to FIG. 7d), causing lever 186 to depress pin 188, thereby actuating switch 187. The effect activating switch 187 is to transfer power from the primary halogen lamp 170 to the replacement halogen lamp 172. Moreover, it will be appreciated that since the engagement of the replacement lamp 172 requires that the knob 174 be pulled out approximately 2½ inches from the front of the panel, a convenient "alert" feature is provided indicating the need to replace the burned out lamp so that the knob 174 can be returned to its original position.

While the above description constitutes the preferred embodiment of the invention, it will be appreciated that the invention is susceptible to modification, variation and change without departing from the proper scope or fair meaning of the accompanying claims.

What is claimed is:

1. In an automated control apparatus for controlling a microsurgical instrument for performing infusion, aspiration and cutting functions of the type used in intraocular surgery, including a first source of infusion fluid hydraulically connected to an infusion line adapted to be connected to a microsurgical instrument, first valve means connected between said first source of infusion fluid and said infusion line for controlling the flow of fluid from said first source of infusion fluid to a microsurgical instrument, and pumping means connected to an aspiration line adapted to be connected to a microsurgical instrument for introducing a suction pressure into said aspiration line; the improvement comprising:

foot switch control means electrically connected to said first valve means, said pumping means, and a microsurgical instrument, for controlling the actuation of said first valve means, the actuation and speed of said pumping means, and the actuation during the cutting mode of operation of said microsurgical instrument, in accordance with the positioning of said foot switch control means, said foot switch control means comprising a multi-position toe pedal switch and a multi-position heel pedal switch mounted to a pivotable base that actuates a first pivot switch when said base is pivoted in one direction and a second pivot switch when said base is pivoted in the opposite direction, such that either of said multi-position toe or heel pedal switches is actuable simultaneously with the actuation of either of said first or second pivot switches without requiring the surgeon to change the position of his foot relative to said pivotable base.

2. The control apparatus of claim 1 further including a second source of infusion fluid hydraulically connected to said aspiration line, and second valve means connected between said aspiration line and said second source of infusion fluid for controlling the flow of fluid from said second source of infusion fluid into said aspiration line; said foot switch control means being electrically connected to said second valve means for controlling the actuation of said second valve means in accordance with the positioning of said foot switch control means.

3. The control apparatus of claim 2 further including circuit means for actuating said second valve means for a relatively brief period of time; said foot switch control means being electrically connected to said circuit means for enabling said circuit means whenever said foot switch control means is positioned for complete cessation of aspiration.

4. The control apparatus of claim 2 further including first transducer means connected to said aspiration line for generating a first audible signal having a characteristic thereof that is varied in accordance with the actual rate of fluid through said aspiration line.

5. The control apparatus of claim 4 further including second transducer means hydraulically connected to said aspiration line for generating a second audible signal perceptively distinguishable from said first audible signal and having a characteristic thereof that is varied in accordance with the amount of suction pressure in said aspiration line.

6. The control apparatus of claim 5 wherein said second transducer means comprises a sterilizable pressure transducer hydraulically connected to said aspiration line, electrical transducer means for generating said second audible signal, and coupling means mechanically connecting said pressure transducer to said electrical transducer means so as to permit said pressure transducer to be readily disconnected from said electrical transducer means.

7. The control apparatus of claim 6 wherein said pressure transducer comprises a diaphragm actuator vacuum pressure device, and said coupling means comprises a receptacle for receiving said pressure transducer so that a mechanical linkage is engaged between a coupling element connected to said diaphragm and a complimentary coupling element connected to said electrical transducer means.

8. The control apparatus of claim 4 wherein said first transducer means comprises photo-detector means for detecting the passage of each drop of aspirate through said aspiration line and electrical transducer means connected to said photo-detector means for generating said first audible sound, said photo-detector means comprising a light emitting device and a photo-electric transducer device positioned on opposing sides of a transparent drip tube hydraulically connected to said aspiration line so that drops of aspirate passing through said drip tube will interrupt the beam of light between said light emitting device and said photo-electric transducer, said electric transducer means being adapted to generate said first audible sound whenever said beam of light is interrupted.

9. The control apparatus of claim 1 wherein said toe and heel pedal switches are three-position switches.

10. An automated control apparatus for controlling a microsurgical instrument for performing infusion, aspiration and cutting functions of the type used in intraocular surgery, including:
   an aspiration line adapted to be connected to a microsurgical instrument;
   pumping means connected to said aspiration line for introducing a suction pressure into said aspiration line;
   first transducer means connected to said aspiration line for continuously monitoring the fluid flow through said aspiration line by generating a first audible signal having a characteristic thereof that is varied in accordance with the actual rate of fluid flow through said aspiration line; and
   second transducer means hydraulically connected to said aspiration line for generating a second audible signal perceptively distinguishable from said first audible signal and having a characteristic thereof that is varied in accordance with the amount of suction pressure in said aspiration line.

11. The control apparatus of claim 10 wherein said first transducer means comprises photo-detector means for detecting the passage of each drop of aspirate through said aspiration line and electrical transducer means connected to said photo-detector means for generating said first audible sound, said photo-detector means comprising a light emitting device and a photoelectric transducer device positioned on opposing sides of a transparent drip tube hydraulically connected to said aspiration line so that drops of aspirate passing through said drip tube will interrupt the beam of light between said light emitting device and said photo-electric transducer, said electric transducer means being adapted to generate said first audible sound whenever said beam of light is interrupted.

12. The control apparatus of claim 10 wherein said second transducer means comprises a sterilizable pressure transducer hydraulically connected to said aspiration line, electrical transducer means for generating said second audible signal, and coupling means mechanically connecting said pressure transducer to said electrical transducer means so as to permit said pressure transducer to be readily disconnected from said electrical transducer means.

13. The control apparatus of claim 12 wherein said pressure transducer comprises a diaphragm actuator vacuum pressure device, and said coupling means comprises a receptacle for receiving said pressure transducer, a coupling element connected to said diaphragm and complimentary coupling element connected to said electrical transducer means, said coupling elements being such that when said pressure transducer is placed in said receptacle said coupling elements are automatically linked together.

14. An automated control apparatus for controlling a microsurgical instrument for performing infusion, aspiration and cutting functions of the type used in intraocular surgery, including:
   an aspiration line adapted to be connected to a microsurgical instrument;
   pumping means connected to said aspiration line for introducing a suction pressure into said aspiration line;
   and transducer means for producing an audible signal having a characteristic thereof that is varied in accordance with the amount of suction pressure in said aspiration line, said transducer means comprising a sterilizable pressure transducer having a pressure responsive actuator hydraulically connected to said aspiration line, electrical transducer means for generating said audible signal, and coupling means mechanically connecting said pressure transducer to said electrical transducer means for transmitting the movement of said pressure responsive actuator to said electrical transducer means, said coupling means comprising a receptacle for receiving said pressure transducer, a coupling element connected to said actuator and a complimentary coupling element connected to said electrical transducer means, said coupling elements being such that when said pressure transducer is placed in said receptacle said coupling elements are automatically linked together.

15. The control apparatus of claim 14 wherein said pumping means comprises a peristaltic suction pump.

16. An automated control apparatus for controlling a microsurgical instrument for performing infusion, aspiration and cutting functions of the type used in intraocular surgery, including:
   a control unit adapted to be connected to a microsurgical instrument comprising
      an infusion line adapted to be connected to a microsurgical instrument, a low pressure source of infusion fluid connected to said infusion line, a high pressure source of infusion fluid hydraulically connected to said infusion line, an aspiration line adapted to be connected to a microsurgical instrument, an intermediate pressure source of infusion fluid hydraulically connected to said aspiration line, first valve means connected between said infusion line and said high pressure source of infusion fluid for controlling the flow of fluid from said high pressure source of infusion fluid to a microsurgical instrument, second valve means connected between said aspiration line and said intermediate pressure source of infusion fluid for controlling the flow of fluid from said intermediate pressure source of infusion fluid into said aspiration line, pumping means having at least two different speeds connected to said aspiration line for introducing a suction pressure into said aspiration line, first transducer means connected to said aspiration line for generating a first audible signal having a characteristic thereof that varies in accordance with the actual rate of fluid flow through said aspiration line, second transducer means hydraulically connected to said aspiration line for generating a second audible signal perceptively distinguishable from said first audible signal and having a characteristic thereof that varies in accordance with the amount of suction pressure in said aspiration line, and circuit means connected to said second valve means for actuating said second valve means for a relatively brief period of time; and a foot switch control unit having at least nine different switch positions that are electrically connected to said control unit such that in a first position said first valve means is opened and the low-speed of said pumping means is actuated, in a second position said first valve means is opened and the high-speed of said pumping means is actuated, in a third position activation of said pumping means is terminated and said first valve means is opened, in fourth, eighth and ninth positions the power is provided for the cutting mode of operation of a microsurgical instrument in combination with the functions performed in said first, second and third positions, respectively, in a fifth position activation of said pumping means is terminated, the power is removed for the cutting mode of operation of a microsurgical instrument and said circuit means is enabled, in a sixth position said second valve means is opened, and in a seventh position said second valve means is opened and the power is provided for the cutting mode of operation of a microsurgical instrument.

17. The control apparatus of claim 16 wherein said foot switch control unit comprises a three-position toe pedal switch and a three-position heel pedal switch mounted to a pivotable base that is applied to actuate a left pivot switch when said base is pivoted to the surgeon's left and a right pivot switch when said base is pivoted to the surgeon's right, such that either of said three-position toe or heel pedal switches is actuable simultaneously with the actuation of either of said left or right pivot switches without changing the position of the surgeon's foot relative to said pivotable base.

18. The control apparatus of claim 17 wherein:

said first position corresponds to said toe pedal switch being initially depressed without pivoting said foot control unit, said second position corresponds to said toe pedal switch being initially depressed and said foot control unit pivoted to the left, said third position corresponds to said toe pedal switch being initially depressed and said foot control unit pivoted to the right.

said fourth position corresponds to said toe pedal switch being fully depressed without pivoting said foot control unit, said fifth position corresponds to said toe and heel pedal switches being fully released, said sixth position corresponds to said heel pedal switch being initially depressed, said seventh position corresponds to said heel pedal switch being fully depressed, said eighth position corresponds to said toe pedal switch being fully depressed and said foot control unit pivoted to the left, and said ninth position corresponds to said toe pedal switch being fully depressed and said foot control unit pivoted to the right.

19. The control apparatus of claim 16 wherein said first transducer means comprises photo-detector means for detecting the passage of each drop of aspirate through said aspiration line and electrical transducer means connected to said photo-detector means for generating said first audible sound, said photo-detector means comprising a light emitting device and a photo-electric transducer device positioned on opposing sides of a transparent drip tube hydraulically connected to said aspiration line so that drops of aspirate passing through said drip tube will interrupt the beam of light between said light emitting device and said photo-electric transducer, said electric transducer means being adapted to generate said first audible sound whenever said beam of light is interrupted.

20. The control apparatus of claim 16 wherein said second transducer means comprises a sterilizable pressure transducer hydraulically connected to said aspiration line, electrical transducer means for generating said second audible signal, and coupling means mechanically connecting said pressure transducer to said electrical transducer means so as to permit said pressure transducer to be readily disconnected from said electrical transducer means.

21. The control apparatus of claim 20 wherein said pressure transducer comprises a diaphragm actuator vacuum pressure device, and said coupling means comprises a receptacle for receiving said pressure transducer so that a mechanical linkage is automatically engaged between a coupling element connected to said diaphragm and a complimentary coupling element connected to said electrical transducer means.

* * * * *